United States Patent [19]

Kamachi et al.

[11] 4,188,320
[45] Feb. 12, 1980

[54] ESTER OF HIGHER FATTY ACID AND REAGENT FOR DETERMINATION OF ACTIVITY OF LIPASE

[75] Inventors: Shinichi Kamachi, Mitaka; Yosuke Ohkura, Fukuoka, both of Japan

[73] Assignee: Chugai Seiyaku Kabushiki Kaisha, Tokyo, Japan

[21] Appl. No.: 943,981

[22] Filed: Sep. 20, 1978

[30] Foreign Application Priority Data

Sep. 22, 1977 [JP] Japan .................. 52-113206

[51] Int. Cl.² .......................... C07C 107/04
[52] U.S. Cl. .................. 260/202; 260/196; 260/197; 435/19
[58] Field of Search .......... 260/202, 196, 207

[56] References Cited

U.S. PATENT DOCUMENTS 2,888,452   5/1959   Schmid et al. ............ 260/202 X
3,986,930   10/1976  Kurooka et al. .......... 195/103.5 R

FOREIGN PATENT DOCUMENTS

50/62686  5/1975  Japan .................. 195/103.5 R
1319411   6/1973  United Kingdom ......... 195/103.5 R

OTHER PUBLICATIONS

Ida, et al., J. Pharm. Soc. Japan, 89, No. 4, 1969, pp. 517-523.

Primary Examiner—Charles F. Warren
Attorney, Agent, or Firm—Browdy and Neimark

[57] ABSTRACT

An ester of higher fatty acid of the formula:

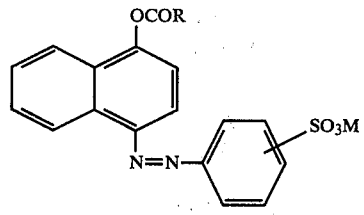

wherein R and M are as defined hereunder, and a reagent for determination of the activity of lipase which contains said ester are disclosed. Such reagent is useful to determine the activity of lipase.

11 Claims, No Drawings

ESTER OF HIGHER FATTY ACID AND REAGENT FOR DETERMINATION OF ACTIVITY OF LIPASE

This invention relates to an ester of higher fatty acid of the formula:

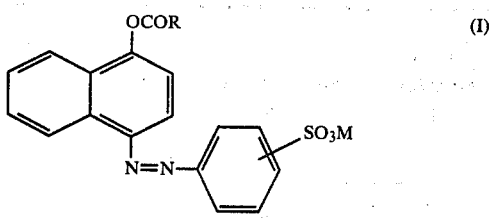

(wherein R is an alkyl group of 9 to 17 carbon atoms; M is an alkali metal) and a reagent for determination of activity of lipase that contains said ester as the effective component.

The end compound of this invention that is represented by formula (I) is prepared, for example, by reacting a compound of the formula:

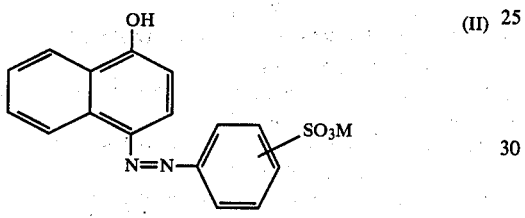

(wherein M is the same as defined above) with a higher fatty acid of the formula RCOOH (III) (R is the same as defined above) or a reactive derivative thereof at a carboxyl group.

Conditions for ordinary esterification may be used for such reaction. Examples of the higher fatty acid of the formula (III) include decanoic acid, lauric acid, myristic acid, palmitic acid, stearic acid, etc., which can be subjected to the reaction either directly or after conversion to reactive derivatives such as acid anhydride, acid halide and so forth. To achieve efficient reaction, a condensation agent such as p-toluenesulfonic acid, dicyclohexyl carbodiimide, or a halogen acceptor such as pyridine, triethyleamine or the like can optionally be used. The end compound may be isolated and purified according to a conventional method. The compound thus obtained is an excellent substrate for determination of the activity of lipase.

Conventionally, olive oil or higher fatty acid esters of phenol or p-nitrophenol and so forth have been used as the substrate for determination of activity of lipase. Determination with olive oil poses problems with purification and quality control of natural oil olive. Another disadvantage of this method results from titration of a liberated fatty acid with alkali. The method of using higher fatty acid esters of phenol or p-nitrophenel is also disadvantageous in that all these synthetic substrates are insoluble in water and are subject to enzymatic reaction in an emulsified state. Therefore, prior to determination, deproteinization is required for suspending the enzymatic reaction and precipitating unreacted synthetic substrate.

The compound according to this invention, however, has a significant advantage in that it obviates the need of deproteinization if it is combined with cholic acid known as an agent for deactivating esterases other than lipase because not only is its specificity to lipase enhanced but it becomes soluble in an aqueous solution.

EXAMPLE 1

A mixture of 3.5g of sodium p-(4-hydroxy-1-naphthylazo)-benzenesulfonate and 7g of lauric anhydride was dissolved in 50 ml of dimethylformamide. After addition of 1 ml of pyridine, the solution was heated until both solutes were completely dissolved, refluxed for about 10 minutes, and cooled. The precipitating crystal was isolated by filtration and recrystallized from dimethylformamide-acetone to produce sodium p-(4-lauryloxy-1-naphthylazo)benzenesulfonate. The yield was 75.2% and the melting point was 300° C. or more (decomposition).

| Elemental analysis | C | H | N |
|---|---|---|---|
| Calculated (%) | 63.1 | 6.3 | 5.3 |
| Found (%) | 62.9 | 6.5 | 5.6 |

EXAMPLES 2 to 6

The procedure of Example 1 was repeated to obtain the following compounds, all of which had a melting point of 300° C. or more (decomposition).

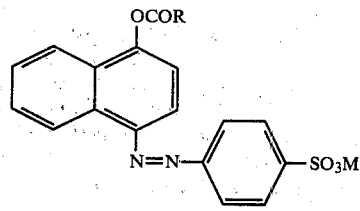

| Ex. No. | R | M | | Elemental analysis | |
|---|---|---|---|---|---|
| | | | | calculated (%) | found (%) |
| 2 | $C_{13}H_{27}-$ | Na | C | 64.3 | 64.1 |
| | | | H | 6.7 | 6.6 |
| | | | N | 5.0 | 4.8 |
| 3 | $C_{15}H_{31}-$ | Na | C | 65.3 | 65.5 |
| | | | H | 7.0 | 7.3 |
| | | | N | 4.8 | 4.7 |
| 4 | $C_{17}H_{35}-$ | Na | C | 66.2 | 66.1 |
| | | | H | 7.4 | 7.2 |
| | | | N | 4.5 | 4.5 |
| 5 | $C_{11}H_{23}-$ | K | C | 61.3 | 61.2 |
| | | | H | 6.1 | 6.0 |
| | | | N | 5.1 | 4.9 |
| 6 | $C_9H_{19}-$ | Na | C | 61.9 | 61.6 |
| | | | H | 5.8 | 5.7 |
| | | | N | 5.6 | 5.6 |

EXAMPLES 7 to 10

The procedure of Example 1 was repeated to produce the following compounds, all of which had a melting point of 300° C. or more (decomposition).

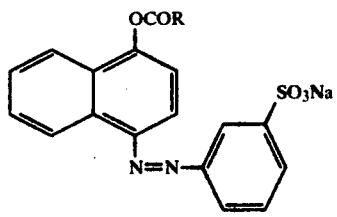

| Ex. No. | R | Elemental analysis | | |
|---|---|---|---|---|
| | | | calculated (%) | found (%) |
| 7 | $C_{11}H_{23}-$ | C | 63.1 | 63.0 |
| | | H | 6.3 | 6.5 |
| | | N | 5.3 | 5.4 |
| 8 | $C_{13}H_{27}-$ | C | 64.3 | 64.1 |
| | | H | 6.7 | 6.6 |
| | | N | 5.0 | 5.1 |
| 9 | $C_{15}H_{31}-$ | C | 65.3 | 65.3 |
| | | H | 7.0 | 7.2 |
| | | N | 4.8 | 4.8 |
| 1: | $C_{17}H_{35}-$ | C | 66.2 | 66.6 |
| | | H | 7.4 | 7.4 |
| | | N | 4.5 | 4.4 |

EXPERIMENT

A substrate solution and a sample lipase were prepared as follows:

Substrate solution: In 106.4 mg of the compound prepared in Example 1 was dissolved 2.5 ml of a 20% sodium cholate aqueous solution to make a total of 10 ml. To 1 ml of the thus obtained solution was added a sodium dodecylsulfate-phosphate buffer (288 mg of sodium dodecylsulfate dissolved in a phosphate buffer (1/15 M, pH 8.0) to make a total of 100 ml) to make a total of 10 ml.

Sample solution: To 2.5 mg of lipase type II (manufactured from hog pancreas lipase by Sigma Chemical Company) was added water to make a total of 25 ml. The solution was diluted to ¼, ½ and ¾ to make samples.

To 1 ml of the substrate solution was added 0.1 ml of each sample and incubated at 37° C. for 30 minutes. After addition of 3 ml of a 10% sodium cholate aqueous solution, the absorbance of the mixture was measured at 475 nm. The results are set forth in the following table.

| Dilution of sample solution | ¼ | ½ | ¾ | 1 |
|---|---|---|---|---|
| absorbance | 0.201 | 0.409 | 0.631 | 0.846 |

We claim:

1. An ester of higher fatty acid of the formula:

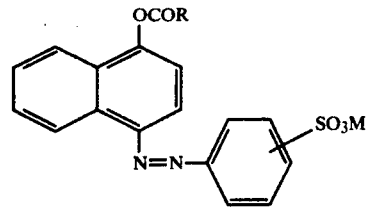

(wherein R is an alkyl group of 9 to 17 carbon atoms; M is an alkali metal).

2. Sodium p-(4-lauroyloxy-1-naphthylazo)benzenesulfonate according to claim 1.

3. Sodium p-(4-myristoyloxy-1-naphthylazo)benzenesulfonate according to claim 1.

4. Sodium p-(4-palmitoyloxy-1-naphthylazo)benzenesulfonate according to claim 1.

5. Sodium p-(4-stearoyloxy-1-naphthylazo)benzenesulfonate according to claim 1.

6. Potassium p-(4-lauroyloxy-1-naphthylazo)benzenesulfonate according to claim 1.

7. Sodium m-(4-lauroyloxy-1-naphthylazo)benzenesulfonate according to claim 1.

8. Sodium m-(4-myristoyloxy-1-naphthylazo)benzenesulfonate according to claim 1.

9. Sodium m-(4-palmitoyloxy-1-naphthylazo)benzenesulfonate according to claim 1.

10. Sodium m-(4-stearoyloxy-1-naphthylazo)benzenesulfonate according to claim 1.

11. Sodium p-(4-capryloxy-1-naphthylazo)benzenesulfonate according to claim 1.

* * * * *